US011221331B2

(12) United States Patent
Van Cleve et al.

(10) Patent No.: US 11,221,331 B2
(45) Date of Patent: Jan. 11, 2022

(54) APPARATUSES AND METHODS FOR MIXING FLUID OR MEDIA BY VIBRATING A PIPETTE USING TRANSIENT AND STEADY-STATE INTERVALS

(71) Applicant: Hycor Biomedical, LLC, Indianapolis, IN (US)

(72) Inventors: Mark Van Cleve, Garden Grove, CA (US); Taylor Reid, Carlsbad, CA (US); Gerold Firl, Poway, CA (US); Yohei Yamamuro, San Diego, CA (US); Nathaniel Hague, Escondido, CA (US)

(73) Assignee: Hycor Biomedical, LLC, Indianapolis, IN (US)

( * ) Notice: Subject to any disclaimer, the term of this patent is extended or adjusted under 35 U.S.C. 154(b) by 258 days.

(21) Appl. No.: 15/890,932

(22) Filed: Feb. 7, 2018

(65) Prior Publication Data

US 2018/0231541 A1 Aug. 16, 2018

Related U.S. Application Data

(60) Provisional application No. 62/458,095, filed on Feb. 13, 2017.

(51) Int. Cl.
| | | |
|---|---|---|
| *G01N 33/543* | (2006.01) | |
| *B01L 3/02* | (2006.01) | |
| *B01L 3/00* | (2006.01) | |
| *G01N 35/10* | (2006.01) | |
| *G01N 1/38* | (2006.01) | |
| *G01N 35/02* | (2006.01) | |
| *G01N 35/00* | (2006.01) | |

(52) U.S. Cl.
CPC ...... *G01N 33/54333* (2013.01); *B01L 3/0227* (2013.01); *B01L 3/0237* (2013.01); *B01L 3/5082* (2013.01); *G01N 1/38* (2013.01); *G01N 35/0098* (2013.01); *G01N 35/025* (2013.01); *G01N 35/10* (2013.01); *G01N 35/1081* (2013.01); *B01L 2300/12* (2013.01); *B01L 2400/043* (2013.01); *G01N 2001/386* (2013.01); *G01N 2035/00534* (2013.01); *G01N 2035/00574* (2013.01); *G01N 2035/1058* (2013.01)

(58) Field of Classification Search
CPC .... B01L 3/0227; B01L 3/0237; B01L 3/5082; B01L 2400/043; B01L 2300/12; G01N 33/5433; G01N 35/1081; G01N 1/38; G01N 35/025; G01N 35/0098; G01N 35/10; G01N 2001/386; G01N 2035/00534; G01N 2035/1058; G01N 2035/00574
See application file for complete search history.

(56) References Cited

U.S. PATENT DOCUMENTS

| | | | |
|---|---|---|---|
| 3,780,992 A * | 12/1973 | Nishi | B01F 11/04 366/114 |
| 4,046,515 A | 9/1977 | de Leeuw | |
| 4,778,279 A | 10/1988 | Bodine | |
| 5,128,103 A | 7/1992 | Wang et al. | |
| 5,736,100 A | 4/1998 | Miyake et al. | |
| 5,811,306 A | 9/1998 | Komatsu | |
| 6,112,603 A | 9/2000 | Pietilae et al. | |
| 6,447,728 B1 | 9/2002 | Wilmes et al. | |
| 6,509,193 B1 | 1/2003 | Tajima | |
| 6,579,724 B2 | 6/2003 | Woodward | |
| 6,592,825 B2 | 7/2003 | Pelc et al. | |
| 6,737,021 B2 | 5/2004 | Watari et al. | |
| 6,767,511 B1 | 7/2004 | Rousseau | |
| 6,818,183 B2 | 11/2004 | Hajduk et al. | |
| 7,201,875 B2 | 4/2007 | Norton et al. | |
| 7,448,287 B2 | 11/2008 | Daniel et al. | |
| 7,544,326 B2 | 6/2009 | Norton et al. | |
| 7,611,837 B2 * | 11/2009 | Yu | C12Q 1/701 424/155.1 |
| 7,670,558 B2 | 3/2010 | Katou et al. | |
| 7,722,815 B2 | 5/2010 | Katou et al. | |
| 7,833,487 B2 | 11/2010 | Sasaki et al. | |
| 7,892,856 B2 | 2/2011 | Grate et al. | |
| 7,955,557 B2 | 6/2011 | Watari et al. | |
| 7,993,934 B2 | 8/2011 | Tabata et al. | |
| 8,079,748 B2 | 12/2011 | Murakami | |
| 8,153,060 B2 | 4/2012 | Nishiki et al. | |
| 8,197,126 B2 | 6/2012 | Tsuda | |
| 8,233,146 B2 | 7/2012 | Chen | |
| 8,317,389 B2 | 11/2012 | Jaegle | |
| 8,496,884 B2 | 7/2013 | Murakami | |
| 8,557,181 B2 | 10/2013 | Hirano | |
| 8,658,102 B2 | 2/2014 | Katou et al. | |
| 8,757,864 B2 | 6/2014 | Yamakawa et al. | |
| 8,873,121 B2 | 10/2014 | Shin et al. | |
| 9,046,505 B2 | 6/2015 | Ebi et al. | |

(Continued)

*Primary Examiner* — Ann Y Lam

(74) *Attorney, Agent, or Firm* — K&L Gates LLP; Louis C. Cullman; Dennis A. Majewski

(57) ABSTRACT

In an embodiment, an immunochemistry analysing system includes a source of paramagnetic particles, a source of fluid, a cuvette configured to receive the paramagnetic particles and the fluid, a pipette configured to (i) translate so that at least a portion of the pipette is located within the cuvette and (ii) dispense at least one of the paramagnetic particles and the fluid into the cuvette so that the paramagnetic particles and the fluid can be mixed within the cuvette, a motor configured to move the pipette while located in the cuvette, and a control unit configured to vary a motor drive of the motor to cause the pipette to mix the fluid with the paramagnetic particles within the cuvette.

17 Claims, 5 Drawing Sheets

(56) References Cited

U.S. PATENT DOCUMENTS

| | | |
|---|---|---|
| 9,291,634 B2 | 3/2016 | Katou et al. |
| 9,302,234 B2 | 4/2016 | Misono |
| 9,359,632 B2 | 6/2016 | Loo et al. |
| 9,678,095 B2 | 6/2017 | Wilmes |
| 9,791,469 B2 | 10/2017 | Wilmes |
| 9,970,952 B2 | 5/2018 | Liu et al. |
| 2003/0078746 A1* | 4/2003 | Samsoondar ........ G01N 21/274 702/66 |
| 2005/0019936 A1* | 1/2005 | Samsoondar ........... B01L 3/508 436/80 |
| 2005/0277184 A1 | 12/2005 | Bargh |
| 2005/0279855 A1* | 12/2005 | Baker .................. G01F 23/266 239/71 |
| 2008/0170463 A1 | 7/2008 | Murakami |
| 2008/0240992 A1 | 10/2008 | Murakami |
| 2009/0027998 A1 | 1/2009 | Halaka et al. |
| 2009/0074621 A1 | 3/2009 | Murakami |
| 2010/0122586 A1 | 5/2010 | Misu |
| 2011/0268628 A1* | 11/2011 | Warhurst .............. B01L 3/0234 422/511 |
| 2012/0164644 A1* | 6/2012 | Neely .................. C12Q 1/6816 435/6.11 |
| 2013/0121880 A1 | 5/2013 | Yamazaki |
| 2014/0341789 A1 | 11/2014 | Wang et al. |
| 2015/0037808 A1 | 2/2015 | Donaty |
| 2015/0130463 A1* | 5/2015 | Wellman ................ G01R 33/30 324/321 |
| 2016/0250609 A1 | 9/2016 | Misono |
| 2017/0014787 A1 | 1/2017 | Douglas et al. |
| 2017/0136456 A1 | 5/2017 | Chen et al. |
| 2017/0197206 A1 | 7/2017 | Lopez |
| 2017/0233798 A1* | 8/2017 | Neely .................. C12Q 1/6895 435/5 |
| 2017/0246601 A1 | 8/2017 | Krufka et al. |
| 2017/0361289 A1* | 12/2017 | Hammerschmidt ........................ B01F 15/0203 |
| 2018/0017590 A1* | 1/2018 | Diamond .............. B03C 1/0332 |
| 2018/0119131 A1* | 5/2018 | Max .................. C12N 15/1006 |

* cited by examiner

APPARATUSES AND METHODS FOR MIXING FLUID OR MEDIA BY VIBRATING A PIPETTE USING TRANSIENT AND STEADY-STATE INTERVALS

PRIORITY CLAIM

This application claims priority to and the benefit of U.S. Provisional Patent Application No. 62/458,095, filed on Feb. 13, 2017, entitled, "Apparatuses and Methods for Mixing Fluid or Media by Vibrating a Pipette Using Transient and Steady-State Intervals," the entire disclosure of which is hereby incorporated by reference and relied upon.

CROSS-REFERENCE TO RELATED APPLICATIONS

The present disclosure is related to PCT/US16/19392, filed Feb. 24, 2016, entitled, "Apparatuses and Methods for Suspending and Washing the Contents of a Plurality of Cuvettes," the entire disclosure of which is hereby incorporated by reference herein.

FIELD OF THE DISCLOSURE

The present disclosure relates generally to methods and apparatuses for mixing a fluid/media using transient and steady-state intervals, and more specifically to a system that vibrates a dispensing pipette within a cuvette using transient and steady-state intervals to mix fluid/media dispensed by the pipette into the cuvette.

BACKGROUND OF THE DISCLOSURE

Many immunochemistry analysis systems require that analyte molecules in a patient's biological sample (e.g. serum or plasma) attach to paramagnetic particles. Such systems require that magnets be positioned so that the paramagnetic particles can be localized and one or more washing steps can be performed to remove background signals associated with potential contaminants and interfering substances that may be present in samples.

When a magnetic force is applied to the paramagnetic particles, however, the magnetic force can cause the paramagnetic particles to cluster, even after the magnetic force is removed. There is accordingly a need for equipment that can mix the paramagnetic particles to break up the clusters so that assays can be performed using the paramagnetic particles. There is also a need for equipment that can perform such mixing without the need for constant calibration.

SUMMARY OF THE DISCLOSURE

The present disclosure is directed to methods and apparatuses for mixing fluid/media using transient and steady-state intervals. In an general example embodiment, an immunochemistry analysing system includes a source of paramagnetic particles, a source of fluid, at least one cuvette configured to receive the paramagnetic particles from the source of paramagnetic particles and the fluid from the source of fluid, at least one pipette configured to (i) translate so that at least a portion of the at least one pipette is located within the at least one cuvette and (ii) dispense at least one of the paramagnetic particles from the source of paramagnetic particles and the fluid from the source of fluid into the at least one cuvette so that the paramagnetic particles and the fluid can be mixed within the cuvette, at least one motor configured to move the at least one pipette while at least a portion of the at least one pipette is located in the at least one cuvette, and a control unit configured to vary a motor drive of the at least one motor to cause the at least one pipette to mix the fluid with the paramagnetic particles within the cuvette.

In another embodiment, the at least one motor moves the at least one pipette by vibrating the at least one pipette.

In another embodiment, the control unit is configured to vary the motor drive of the at least one motor by operating the at least one motor using alternating transient and steady-state intervals.

In another embodiment, the control unit is configured to reverse the motor at least one time to mix the fluid with the paramagnetic particles within the cuvette.

In another embodiment, the control unit is configured to vary the motor drive of the at least one motor by increasing a magnitude of the motor drive of the at least one motor at least one time.

In another embodiment, the control unit is configured to vary the motor drive of the at least one motor by decreasing a magnitude of the motor drive of the at least one motor at least one time.

In another embodiment, the source of fluid includes at least one of a patient sample, a capture reagent and a rinse buffer.

In a general example embodiment, a method of mixing paramagnetic particles includes injecting paramagnetic particles into a cuvette, applying a magnetic force outside of the cuvette to attract the paramagnetic particles to a wall of the cuvette, and varying a motor drive of a motor to cause a mixing mechanism within the cuvette to mix the paramagnetic particles within the cuvette.

In another embodiment, the mixing mechanism is a pipette, and the method includes injecting a fluid into the cuvette with the pipette.

In another embodiment, the method includes injecting the fluid into the cuvette with the pipette after applying the magnetic force.

In another embodiment, the mixing mechanism is a pipette, and the method includes injecting the paramagnetic particles into the cuvette with the pipette.

In another embodiment, varying the motor drive of the motor includes operating the at least one motor using alternating transient and steady-state intervals.

In another embodiment, varying the motor drive of the motor includes varying a magnitude of the motor drive for at least two different steady-state time intervals.

In another embodiment, the method includes reversing the motor at least one time to mix the paramagnetic particles within the cuvette.

In another embodiment, increasing a magnitude of the motor drive of the at least one motor at least one time In another embodiment, includes decreasing a magnitude of the motor drive of the at least one motor at least one time.

In a general example embodiment, an immunochemistry analysing system includes a source of paramagnetic particles, a cuvette configured to receive paramagnetic particles from the source of paramagnetic particles, a mixing mechanism configured to be at least partially submerged within the cuvette, a motor configured to vibrate the mixing mechanism, a memory storing at least one mixing setting in which a motor drive of the motor is varied over a series of time intervals, and a control unit configured to operate the motor according to the at least one mixing setting to cause the mixing mechanism to mix the paramagnetic particles within the cuvette.

In another embodiment, the mixing mechanism is a pipette configured to dispense fluid into the cuvette to be mixed with the paramagnetic particles.

In another embodiment, the mixing mechanism is a pipette configured to dispense the paramagnetic particles into the cuvette.

In another embodiment, the at least one mixing setting includes instructions to operate the motor using alternating transient and steady-state intervals.

In another embodiment, the at least one mixing setting includes instructions to increase a magnitude of the motor drive of the motor during the steady-state intervals.

In another embodiment, the at least one mixing setting includes instructions to increase a magnitude of the motor drive of the motor during one steady-state time interval and/or decrease the magnitude of the motor drive of the motor during another steady-state time interval.

In another embodiment, the at least one mixing setting includes instructions to reverse the motor during at least one of the steady-state time intervals.

In a general example embodiment, a mixing system includes at least one cuvette, at least one pipette configured to (i) translate so that at least a portion of the at least one pipette is located within the at least one cuvette and (ii) dispense at least one of fluid or media into the cuvette so that the at least one of fluid or media can be mixed within the cuvette, at least one motor configured to move the at least one pipette while at least a portion of the at least one pipette is located in the at least one cuvette, and a control unit configured to vary a motor drive of the at least one motor to cause the at least one pipette to mix the at least one of fluid or media within the cuvette.

In a general example embodiment, a mixing system includes a cuvette, a mixing mechanism configured to be at least partially submerged within the cuvette, a motor configured to vibrate the mixing mechanism, a memory storing at least one mixing setting in which a motor drive of the motor is varied over a series of time intervals, and a control unit configured to operate the motor according to the at least one mixing setting to cause the mixing mechanism to mix a substance within the cuvette.

BRIEF DESCRIPTION OF THE DRAWINGS

Embodiments of the present disclosure will now be explained in further detail by way of example only with reference to the accompanying figures, in which.

DETAILED DESCRIPTION

Before describing in detail the illustrative system and method of the present disclosure, it should be understood and appreciated herein that the present disclosure relates to methods and apparatuses that perform diagnostic assays for different types of analyte molecules of interest, specifically for molecules that bind to immunogens. In general, the system utilizes common paramagnetic particles, for example magnetic beads or microparticles, that are pulled to the wall of a reaction cuvette by magnets during a washing process so that liquid can be aspirated from the cuvette. Disclosed herein is an advantageous system and method for mixing the paramagnetic particles. It is also contemplated that the present disclosure can also be applied to fluid dispensing and/or mixing systems that do not utilize paramagnetic particles.

As explained in more detail below, using the illustrative system and method of the present disclosure, paramagnetic particles can be coated with one or more capture reagent that will eventually bind analyte molecules of interest in a patient's blood sample. In example embodiments, the capture molecule is an immunogen which binds an immunogen-binding molecule (analyte), such as an antibody, in the patients' blood sample. After the capture reagents bind to the paramagnetic particles and the cuvettes undergo a washing process, a patient sample, and optionally a diluent if needed, can be added to the particles in the reaction cuvette and incubated. This allows analytes of interest in the patient's blood sample to bind to one or more capture reagent that has in turn been bound to the surface of a paramagnetic particle. After a patient sample incubation period, another washing process can be performed to remove any excess or unbound sample, and then a conjugate and a luminescent label can be added to the cuvette. When added to the cuvette, it can be expected that some portion of the conjugate will bind to the capture reagent/sample complex on the paramagnetic particles after an incubation period. The particles then undergo another wash process to remove any unbound conjugate, and then a luminescent label is added to the reaction cuvette and incubated for a short period of time to allow the chemiluminescent glow reaction to reach equilibrium. After equilibrium is reached, luminescence and fluorescence readings of the sample can be taken to perform an assay.

Figure 1:
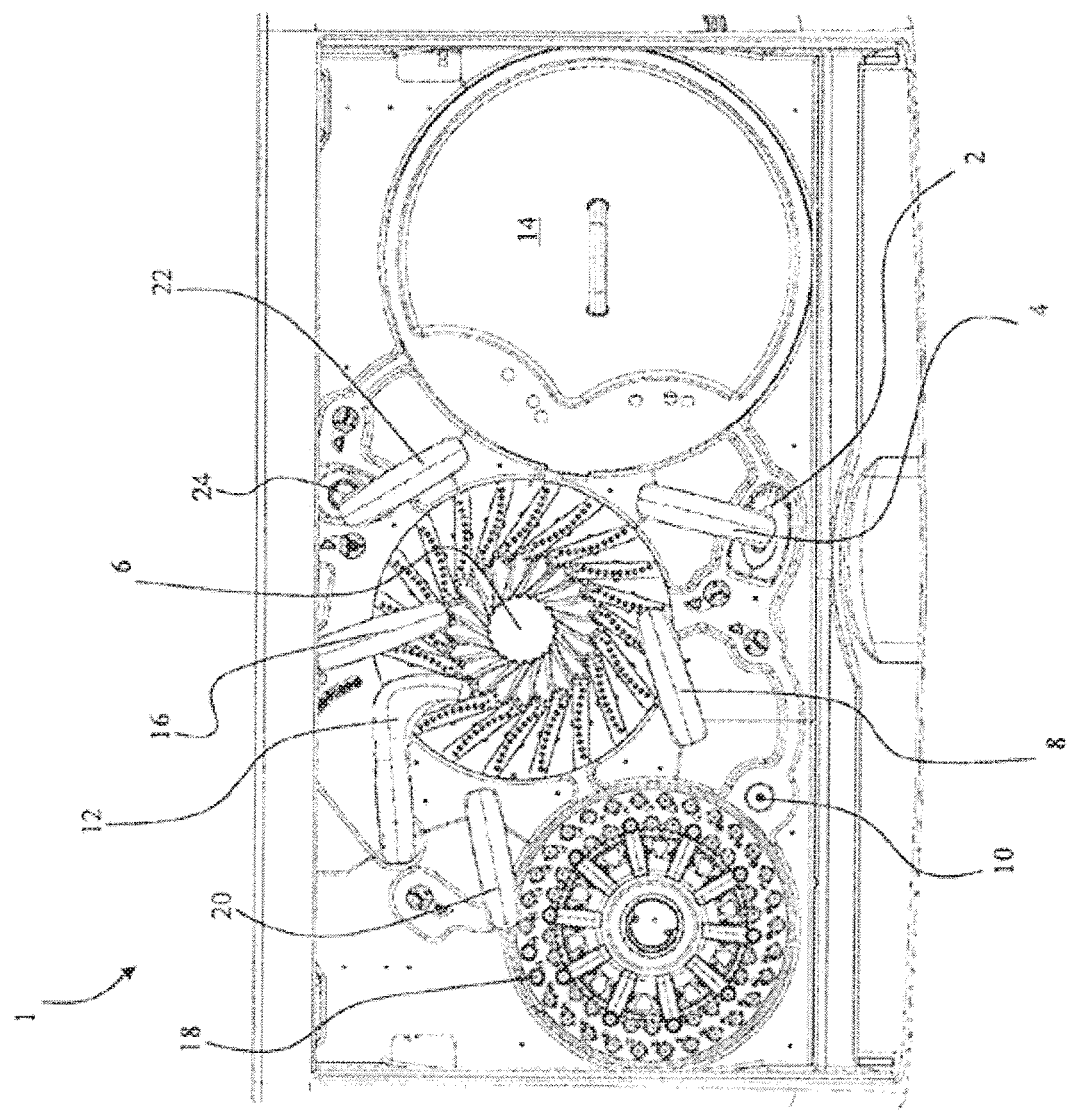
FIG. 1 is a top plan view of an example embodiment of an automated immunochemistry analyzer and reagent system according to the present disclosure.

FIG. 1 illustrates various components of an example embodiment of an automated immunochemistry analyzer 1 according to the present disclosure. Automated immunochemistry analyzer 1 can take an analyte sample, create an environment that will allow it to bind to a paramagnetic particle, perform a number of washing steps, and then quantify and normalize the luminescence signal of the analyte sample. This can be accomplished through an automated process that utilizes a vortexer 2, an R1 pipettor 4, a reaction rotor 6, an optics pipettor 8, an optics device 10, a multi rinse pipettor 12, a reagent rotor 14, a single rinse pipettor 16, a sample rotor 18, a sample pipettor 20, an R2 pipettor 22, and a mixed substrate container 24.

In one embodiment disclosed herein, an apparatus such as automated immunochemistry analyzer 1 can quantify and normalize the luminescence signal of an analyte sample before reaction of the analyte with the capture reagent. In an embodiment, automated immunochemistry analyzer 1 begins by first dispensing fluorescently labelled paramagnetic particles, or fluo-beads, into a cuvette 50 located within the reaction rotor 6. The fluo-beads can be initially located in vortexer 2 and transferred to reaction rotor 6 by R1 pipettor 4. R1 pipettor 4 can aspirate a desired quantity of the fluo-bead mixture and transfer the aspirated quantity to reaction rotor 6 where it is injected into a cuvette 50 of reaction rotor 6. Optics pipettor 8 can then aspirate a test sample from the cuvette 50 of reaction rotor 6 and transfer the test sample to optics device 10, where fluorescence and luminescence measurements can be recorded. The initial recording of the fluorescence and luminescence signal can be used as a baseline measurement for the initial concentration of fluo-beads in a sample. After recording the measurements, multi rinse pipettor 12 can rinse the cuvettes 50 using a wash buffer.

In order to prepare the analytical substrates, fluo-beads can be transferred from vortexer 2 to a cuvette 50 in reaction rotor 6 via R1 pipettor 4. R1 pipettor 4 can also aspirate one or more capture reagent from reagent rotor 14 and inject the one or more capture reagent into the cuvette 50. After an incubation period, single rinse pipettor 16 can inject a rinse buffer to stop the capture reagent binding reaction with precise timing. A substantial amount of the suspended fluo-bead can then be localized by magnets within the reaction rotor 6 over a period of time. After the magnets have substantially localized the fluo-beads within the cuvette 50, multi rinse pipettor 12 can aspirate and dispose of a portion of the rinse buffer, leaving a portion of the fluo-beads localized within the cuvette 50. Multi rinse pipettor 12 can proceed to inject a wash buffer into the cuvette 50 of reaction rotor 6, resuspending the fluo-beads. The fluo-beads can again be localized by the magnets within reaction rotor 6 to be followed by multi rinse pipettor 12 aspirating and discarding a portion of the sample that was not localized from the cuvette 50 in the reaction rotor 6. Thus, any unbound capture reagent is removed from the cuvette 50.

A patient sample can be contained in a sample tube in sample rotor 18. The patient sample can further be partially diluted with a sample diluent. At this point, sample pipettor 20 can aspirate a portion of the patient sample and inject the patient sample into the cuvette 50 of reaction rotor 6 to resuspend the fluo-beads. The cuvette 50 containing the patient sample within the reaction rotor 6 can then incubate the patient sample. In one embodiment, for example, the incubation temperature can be about 37° C.+/− about 0.2° C., while the incubation time can be about 37.75 minutes+/− about 2 minutes. After incubation, multi rinse pipettor 12 can inject the rinse buffer to again resuspend the fluo-beads. Another localization process is performed by reaction rotor 6 by allowing the fluo-beads to substantially collect within the cuvette 50 near the magnets in reaction rotor 6. After the localization of the fluo-beads, multi rinse pipettor 12 can aspirate and discard a portion of the fluid within the cuvette 50 of reaction rotor 6 that was not localized during the localization process.

Multiple rinse cycles can then be performed on the sample within the cuvette 50 of reaction rotor 6. The rinse cycles can be performed using multi rinse pipettor 12 to inject a wash buffer into the cuvette 50 to resuspend the fluo-beads. Another localization step can allow the fluo-beads to collect within the cuvette 50 by the magnets within reaction rotor 6. After about a 90 second fluo-beads collection period, multi rinse pipettor 12 can aspirate and discard a portion of the wash buffer, leaving a substantial portion of the fluo-beads within the cuvette 50 of the reaction rotor 6. Another rinse cycle can then occur using multi rinse pipettor 12 to again inject wash buffer into the cuvette 50 and allow the fluo-beads to resuspend. Another fluo-bead localization process can utilize the magnets within the reaction rotor 6 to localize the fluo-beads from the rest of the sample. Finally, the multi rinse pipettor 12 can aspirate a portion of the sample that was not localized by the localization process.

At this point, R1 pipettor 4 can aspirate a conjugate contained in a conjugate cuvette within reagent rotor 14. R1 pipettor 4 can then inject the previously aspirated conjugate into the cuvette 50 of the reaction rotor 6. After incubating the cuvette 50 under controlled time and temperature in reaction rotor 6, multi rinse pipettor 12 can inject a rinse buffer into the cuvette 50 in reaction rotor 6. Another fluo-bead localization cycle can be performed by allowing magnets within reaction rotor 6 to substantially localize the fluo-beads within the cuvette 50. Multi rinse pipettor 12 can aspirate and discard a portion of the sample within the cuvette 50 that has not been localized during the localization cycle.

Multiple rinse cycles can be performed on the sample within the cuvette 50 of reaction rotor 6. Multi rinse pipettor 12 can inject a wash buffer to resuspend the fluo-beads within the cuvette 50. Another fluo-bead localization cycle can localize the fluo-beads by locating the cuvette 50 within close proximity to the magnets in reaction rotor 6 over an adequate period of time. After the localization cycle, multi rinse pipettor 12 can aspirate and discard a portion of the sample that was not localized during the localization cycle. Another wash cycle can then occur by using multi rinse pipettor 12 to inject the wash buffer to resuspend the fluo-beads. Another localization cycle can utilize the magnets within reaction rotor 6 to localize the fluo-beads within the cuvette 50. After the localization process, multi rinse pipettor 12 can again aspirate and discard a portion of the sample that was not localized during the localization cycle.

R2 pipettor 22 can then aspirate a substrate or a mixed substrate sample from the mixed substrate container 24 and inject the substrate or mixed substrate sample into the cuvette 50 of the reaction rotor 6, resuspending the fluo-bead with the mixed substrate sample. The sample is then incubated for a period of time. The sample in the cuvette 50 of reaction rotor 6 can then be aspirated by optics pipettor 8 and placed in optics device 10. After optics device 10 makes fluorescence and luminescence optical observations, the sample is discarded and the multi rinse pipettor rinses the cuvettes 50 of reaction rotor 6 in preparation for the next test.

Figure 2:
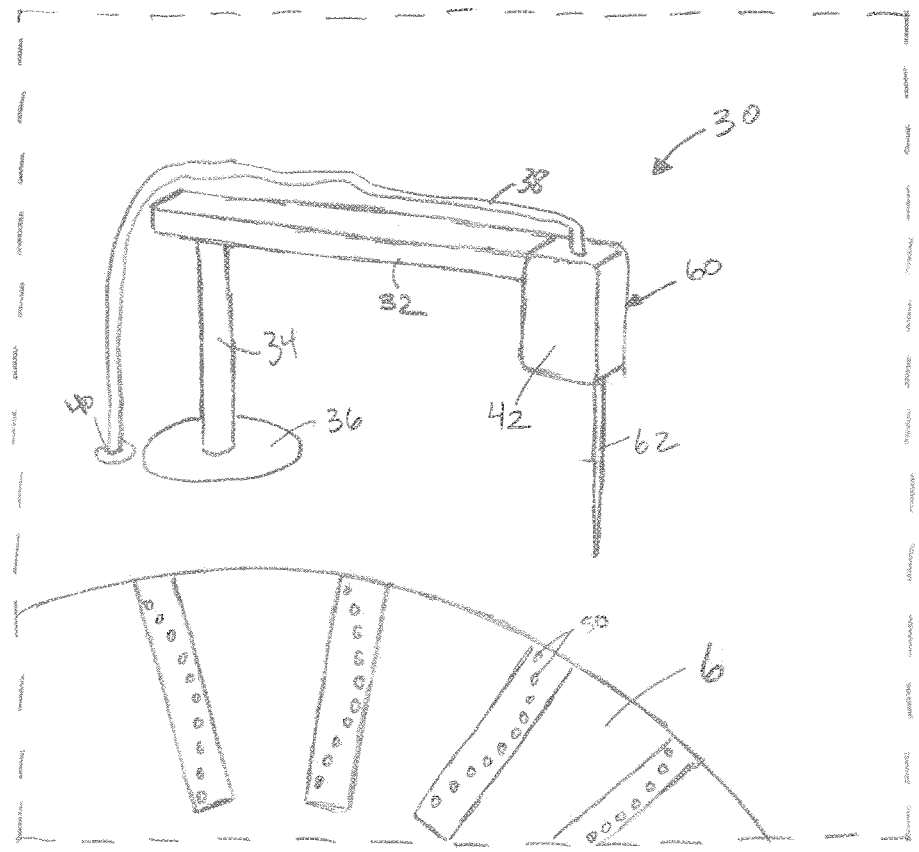
FIG. 2 is a perspective view of an example embodiment of a fluid dispensing and mixing system that can be used as a pipettor in FIG. 1.
Figure 3:
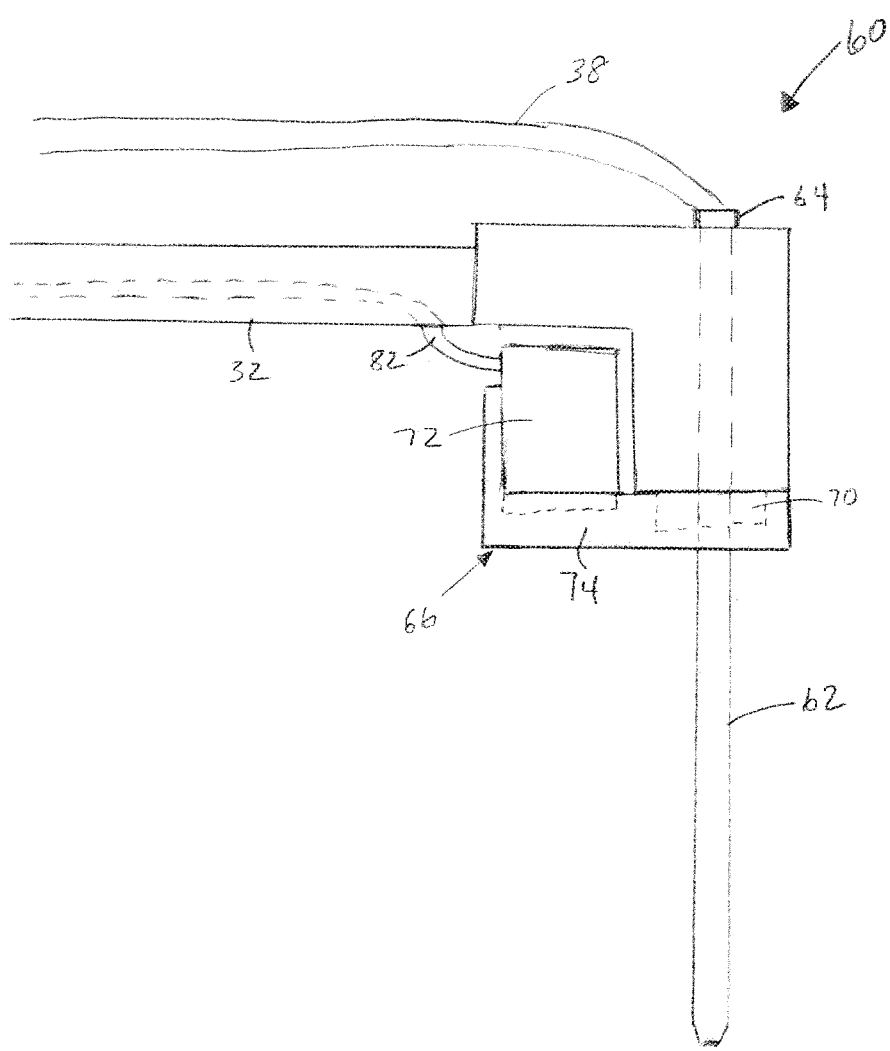
FIG. 3 is a detailed side view of an example embodiment of the fluid dispensing and mixing mechanism at the end of the fluid dispending and mixing system of FIG. 2.
Figure 3:
Figure 4:
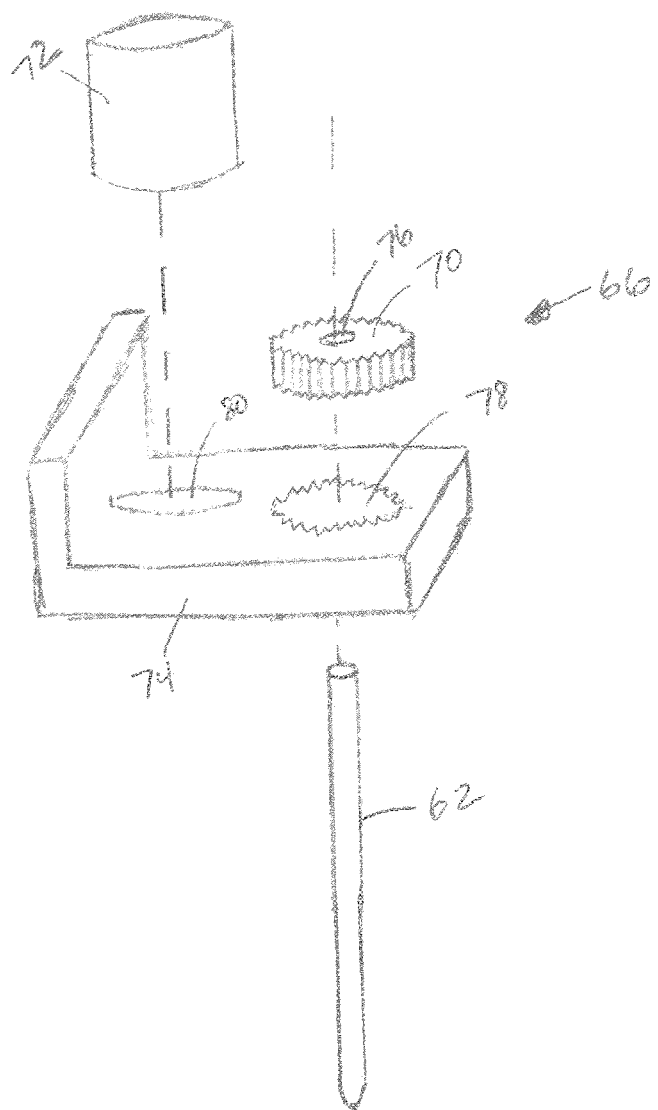
FIG. 4 is an exploded perspective view of an example embodiment of the vibrational assembly shown in FIG. 3.

One issue that can arise when using paramagnetic particles, or flow-beads, in a device such as the automated immunochemistry analyzer 1 shown in FIG. 1 is that the paramagnetic particles can cluster at the sides of the cuvette 50 after the magnetic force is applied to the cuvette 50. To break up the paramagnetic particles, any one or more of R1 pipettor 4, optics pipettor 8, multi rinse pipettor 12, single rinse pipettor 16, sample pipettor 20 and R2 pipettor 22 illustrated in the embodiment of FIG. 1 can be configured as a fluid dispensing and mixing system 30 that mixes the paramagnetic particles within one or more cuvette 50 within reaction rotor 6. FIGS. 2 to 4 illustrate an example embodiment of such a fluid dispensing and mixing system 30 according to the present disclosure. It should be understood that every element in FIGS. 2 to 4 could also be shown in FIG. 1 but has been omitted from FIG. 1 for simplicity.

In the illustrated embodiment, fluid dispensing and mixing system 30 includes an arm 32 attached to a rod 34 that rotates around a base 36, and at least one tube 38 enabling a positive or negative pneumatic force to be used to aspirate and/or dispense a fluid sample from a fluid dispensing and mixing mechanism 60 located at the end of arm 32, and/or enabling a fluid be delivered from a fluid reservoir (not shown) located at an opposite end 40 of tube 38 to the fluid dispensing and mixing mechanism 60. In the illustrated embodiment, only a single tube 38 is shown to be running outside of arm 32 for illustrative purposes, but it should be understood that the design can be simplified by running tube 38 (or multiple tubes 38) through arm 32 and/or rod 34 so that the tube 38 is not exposed.

FIG. 3 shows a detailed view of the fluid dispensing and mixing mechanism 60 at the end of arm 32 without the cover 42 shown in FIG. 2. Fluid dispensing and mixing mechanism 60 functions to dispense and mix fluid within one or more cuvette 50 held by reaction rotor 6. In the illustrated embodiment, fluid dispensing and mixing mechanism 60 includes a pipette 62, a tube inlet 64, and a vibrational assembly 66. In use, and as explained in more detail below, tube inlet 64 receives a positive or negative pneumatic force via tube 38 to cause pipette 62 to aspirate and/or dispense a fluid sample. In an embodiment, tube 38 can also be used to aspirate and/or dispense the fluid itself via pipette 62. For example, if fluid dispensing and mixing mechanism 60 is used as the multi rinse pipettor 12 or single rinse pipettor 16 discussed above, tube 38 can be connected to a source of rinse buffer at end 40 so that the rinse buffer can be delivered to pipette 62 for injection into a cuvette 50. A second tube 38 can also be included to aspirate the rinse buffer from pipette 62. In another example, if fluid dispensing and mixing mechanism 60 is used as R1 pipettor 4, optics pipettor 8, sample pipettor 20 or R2 pipettor 22, a pneumatic force can be used to cause pipette 62 to aspirate fluid or paramagnetic particles from one location (e.g., a cuvette of a rotor) and dispense the fluid or paramagnetic particles in another location (e.g., another cuvette of another rotor).

FIG. 4 shows an exploded view of vibrational assembly 66. In the illustrated embodiment, vibrational assembly 66 includes a knurled shaft 70, a motor 72 and a vibration translating base member 74. In an embodiment, an aperture 76 in the center of knurled shaft 70 can be placed around pipette 62, and knurled shaft 70 can then be placed into a corresponding indentation or aperture 78 in base member 74. The matching features of the knurled shaft 70 and aperture 76 allow base member 74 to be secured to knurled shaft 70 at a specific radial position and transmit any motion or vibration of base member 74 to pipette 62. Motor 72 can be secured in a corresponding indentation or aperture 80 in base member 74.

In the illustrated embodiment, motor 72 receives a voltage and/or is controlled via a wire 82 running through arm 32, but those of ordinary skill in the art will also recognize other ways to control and/or provide a voltage to motor 72. When a voltage is provided to motor 72, the voltage causes motor 72 to rotate an eccentric mass which imparts a vibration to motor 72 and any other components secured to motor 72 such as base member 74. The vibrations are then transferred to pipette 62 via base member 74 and/or knurled shaft 70. The vibrations translated to pipette 62 can be used to mix a fluid sample within a cuvette 50 and/or break up a cluster of paramagnetic particles within a cuvette 50. The motor 72 can be, for example, a brushed DC motor, a brushless DC motor, a stepper motor, or the like. In an embodiment, the motor can include a linear actuator such as a piezoelectric actuator to stimulate vibration or motion of pipette 62.

In an embodiment, automated immunochemistry analyzer 1 can also include a graphical user interface ("GUI") and a control unit that work together to allow a user to enter instructions into and/or control automated immunochemistry analyzer 1. The GUI and the control unit can accompany or be a part of automated immunochemistry analyzer 1, or can be located remotely from automated immunochemistry analyzer 1 and communicate with automated immunochemistry analyzer 1 via a wireless or wired data connection. In another embodiment, the GUI and the control unit can be entirely separate from automated immunochemistry analyzer 1. The control unit can include a processor and a memory, which can include a non-transitory computer readable medium. In an embodiment, the memory can store mixing settings such as those described below, and the control unit can operate automated immunochemistry analyzer 1 in accordance with the mixing settings.

Figure 5:
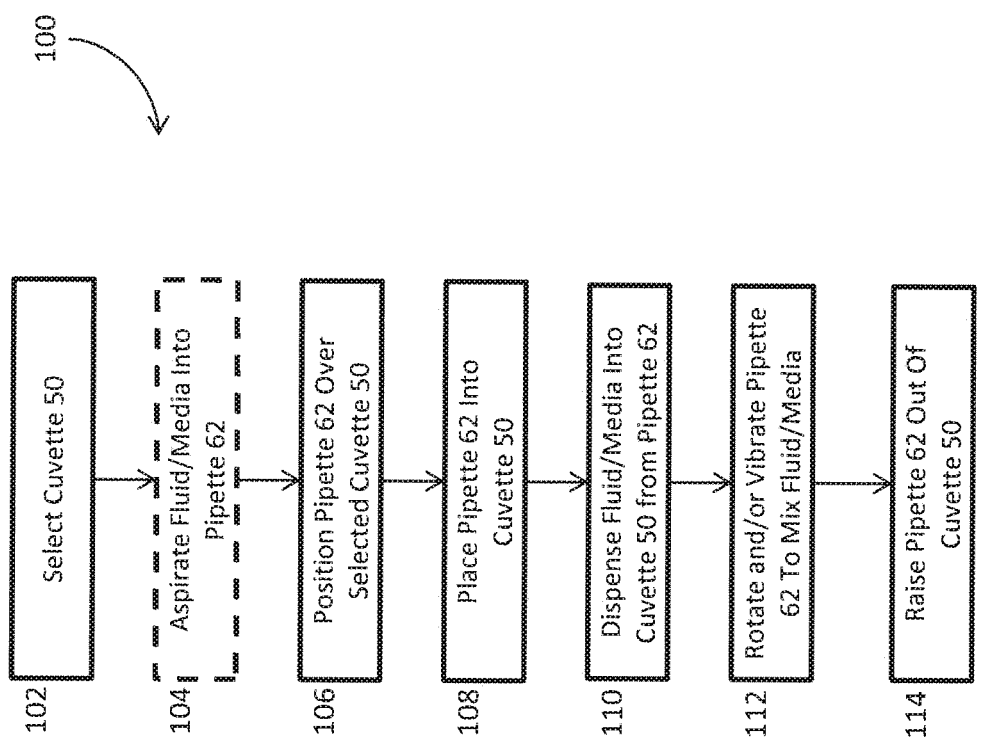
FIG. 5 illustrates an example embodiment of a control method that can be performed by the fluid dispensing and mixing system of FIG. 2.

FIG. 5 shows a control method 100 for using fluid dispensing and mixing system 30 with automated immunochemistry analyzer 1. The control method can be performed automatically by the control unit, which can control the movement of fluid dispensing and mixing system 30 and the individual elements thereof according to instructions entered into the GUI by a user. For example, the control unit can include a database with the locations of fluids and paramagnetic particles stored within the rotors of automated immunochemistry analyzer 1, and can cause fluid dispensing and mixing system 30 to rotate and translate pipette 62 to the locations depending on the type of assay being run by the user. The control unit can also control the amount of voltage delivered to motor 72 to vibrate pipette 62, and can control the pneumatic force and/or fluid sent through one or more tube 38.

In an embodiment, control method 100 begins after paramagnetic particles have already been dispensed within a cuvette, and after a magnetic force has been applied to the cuvette 50 which has caused the paramagnetic particles to cluster. For example, R1 pipettor 4 can dispense paramagnetic particles into cuvette 50 and then a magnetic force can be applied to cuvette 50. Control method 100 can then be performed by dispensing another fluid into cuvette 50 with R1 pipettor 4 or any of the other pipettors discussed above. In another embodiment, pipette 62 can dispense and mix the paramagnetic particles in accordance with control method 100. For example, R1 pipettor 4 can dispense the paramagnetic particles into cuvette 50 and then mix the paramagnetic particles before or after a magnetic force is applied to cuvette 50.

At step 102 of control method 100, a cuvette 50 within reaction rotor 14 is selected for the disbursement of fluid/media. The selection can be made by a user or can automatically be made by a control unit. In an embodiment, a user can simply select a desired assay to be run on a patient sample via the GUI, and the control unit can select an appropriate cuvette based on the selected assay and/or based on an available cuvette 50.

Optionally, at step 104, the control unit can cause pipette 62 to aspirate fluid/media from a rotor of automated immunochemistry analyzer 1, for example, by applying a negative pneumatic force to tube 38 to draw the fluid/media into pipette 62. The fluid can be, for example, a patient sample, a capture reagent or a rinse buffer. The media can be, for example, paramagnetic particles. For example, in an embodiment in which sample pipettor 20 includes fluid dispensing and mixing system 30, pipette 62 can aspirate a patient sample from sample rotor 18 so that the patient sample can then be injected into cuvette 50. Step 104 can be skipped, for example, in an embodiment in which fluid dispensing and mixing mechanism 60 is used as the multi rinse pipettor 12 or single rinse pipettor 16 discussed above and tube 38 is connected to a source of rinse buffer at end 42 so that the rinse buffer can be delivered to pipette 62 for injection into a cuvette 50.

At step 106, pipette 62 is positioned over the selected cuvette 50. The positioning can be accomplished by rotating and/or translating pipette 62 to be located over the selected cuvette 50, by rotating and/or translating cuvette 50 to be located under pipette 62, or by rotating and/or translating both of pipette 42 and cuvette 50 as shown in the illustrated embodiment. The rotation and translation can be automatically controlled by the control unit. In the illustrated embodiment, rod 34 rotates about base 36 to rotate pipette 62 at the end of arm 32 to be located at different positions over reaction rotor 14, while reaction rotor 14 rotates to locate cuvettes 50 near arm 32.

At step 108, the tip of pipette 62 is placed into cuvette 50. The placement of pipette 62 into cuvette 50 can be accomplished by lowering pipette 62 and/or by raising cuvette 50. In the illustrated embodiment, cuvette 50 remains stationary once positioned underneath pipette 62, and pipette 62 is lowered into cuvette 50. In the illustrated embodiment, rod 34 is translated upward and downward with respect to base 36 to translate pipette 62 upward and downward. In an alternative embodiment, fluid dispensing and mixing mechanism 60 can include a translational assembly having a motor that lowers pipette 62 into cuvette 50 while the rest of fluid dispensing and mixing system 30 remains stationary.

At step 110, fluid/media is dispensed from pipette 62 into cuvette 50. The fluid/media can be dispensed, for example, by the control unit causing a positive pneumatic force to be applied through tube 38, or by the control unit causing a fluid be delivered from a fluid reservoir through tube 38. In an embodiment, cuvette 50 already contains paramagnetic particles at this point and the paramagnetic particles have already been subjected to a magnetic force which has caused the paramagnetic particles to cluster within cuvette 50. For example, in an embodiment in which sample pipettor 20 includes fluid dispensing and mixing system 30, pipette 62 can inject a patient sample from sample rotor 18 into cuvette 50 so that the patient sample can attach to the paramagnetic particles due to the presence of a capture reagent. In another embodiment, in which sample R1 pipettor 4 and/or R2 pipettor 22 includes fluid dispensing and mixing system 30, pipette 62 can inject a capture reagent into cuvette 50 so that the capture reagent can attach to the paramagnetic particles. In other embodiments, pipette 62 injects the paramagnetic particles into cuvette 50 and then mixes the paramagnetic particles within cuvette 50, pipette 62 injects a rinse buffer into cuvette 50, or pipette 62 injects and mixes fluid as it is moving vertically to minimize contact of the sample with the outer surface of pipette 62.

At step 112, pipette 62 remains within cuvette 50 so that at least a portion of pipette 62 is submerged below the surface of the fluid/media located in cuvette 50. The control unit then causes a voltage to be delivered to motor 72 via wire 82 to cause pipette 62 to vibrate to mix the fluid/media within cuvette 50. In an embodiment, and as explained in more detail below, the control unit can cause the magnitude of the motor 72 to be varied and/or send voltage to the motor in intervals to perform optimal mixing. The vibration of pipette 62 breaks up any clustering of the paramagnetic particles already located within cuvette 50 or injected into cuvette 50 via pipette 62 and/or causes the fluid dispensed by pipette 62 to be mixed with the paramagnetic particles At step 114, pipette 62 is removed from cuvette 50. The removal of pipette 62 from cuvette 50 can be accomplished by raising pipette 62 and/or by lowering cuvette 50. In the illustrated embodiment, cuvette 50 remains stationary, and pipette 62 is raised from cuvette 50 by translating rod 34 upward with respect to base 36. In an alternative embodiment, a translational assembly can raise pipette 62 from cuvette 50 while the rest of fluid dispensing and mixing system 30 remains stationary.

One issue that arises with the use of motor 72 is that different motors 72 can operate slightly differently requiring calibration of each motor 72 when installed, and the power of any individual motor 72 can also decline over the life of motor 72. It has been determined that performing step 112 by vibrating pipette 42 using transient and/or steady-state intervals works particularly well when the mixture within cuvette 50 includes paramagnetic particles, and also allows for a uniform mixing setting that can be used without motor 72 having to be calibrated before the mixing occurs. The use of transient and/or steady-state intervals also prevents the need for recalibration due to declining motor performance over the life of a motor 72.

In an embodiment, the control unit causes vibrational assembly 66 to vibrate pipette 62 by varying the motor drive of motor 72 in steady-state intervals to cause the vibration of pipette 62 to increase and/or decrease in a stepwise fashion. In the examples described below, varying the motor drive includes varying the pulse width modulation ("PWM") of motor 72. In other embodiments, varying the motor drive can include, for example, using direct voltage control, current control, servo-control, or the like. Those of ordinary skill in the art will recognize other ways to vary the motor drive of motor 72.

The intervals can occur consecutively or can be interspaced with transient intervals in which motor 72 of vibrational assembly 66 is not operated or operates at 0 PWM. Several examples of transient and steady-state intervals are set forth below. As used herein, "pulse width modulation" is used to describe how the motor 72 is adjusted. A 100% pulse width modulation, as used below, represents input voltage applied to the motor for the entire time interval, whereas a 0% pulse width modulation represents no input voltage provided to the motor or the motor being turned off during the time interval. For example, a 50% pulse width modulation over a 100 ms time interval would mean that input voltage is applied to the motor for 50 ms of the 100 ms interval. In an embodiment, the voltage being applied to the motor below for a longer period of time results in higher magnitude mixing power being generated by the motor during the time interval. In another embodiment, the values shown below can represent a magnitude of total motor power applied during the time interval, meaning that the magnitude of the total motor power is increased or decreased as shown in the intervals. The following description uses pulse width modulation percentages to describe how the motor is controlled in comparison to the maximum possible for a given input voltage to the motor. It should be understood that different pulse width modulation percentages or magnitude values besides those described below will be used with different types of motors. The patterns using different transient and steady-state intervals and different increases/decreases in magnitudes according to the examples below will be applicable to different types of motors that have different outputs.

Table 1 illustrates a mixing setting in which the PWM of motor 72 of vibrational assembly 66 alternates between transient and steady-state intervals, with the steady-state intervals increasing in a constant manner as the mixing progresses.

TABLE 1

| | Time (ms) | | | | | | | | |
|---|---|---|---|---|---|---|---|---|---|
| | 0 | 100 | 120 | 220 | 240 | 340 | 360 | 460 | 480 | 580 |
| PWM (%) | 14 | 0 | 15 | 0 | 16 | 0 | 17 | 0 | 18 | 0 |

In Table 1, the steady-state intervals are each 100 ms and the transient intervals are each 20 ms, meaning that the pipette 62 alternates between vibrating during the 100 ms intervals and not vibrating during the 20 ms intervals. At 0 ms, the process begins by applying a 14% PWM. Pipette 62 is then transient from the 100 ms mark to the 120 ms mark, and the PWM is changed to 15% at the 120 ms mark. As shown in Table 1, the PWM is continuously increased 1% at each steady-state interval marker.

In an embodiment, the magnitude of power of the motor is increased or decreased according to the rising or lowering PWM values shown above. In an embodiment, in Table 1, a first vibrational magnitude is applied by motor 72, then a transient interval occurs, then a second magnitude greater than the first magnitude is applied, then a transient interval occurs, then a third magnitude greater than the second magnitude is applied, then a transient interval occurs, then a fourth magnitude greater than the third magnitude is applied, then a transient interval occurs, and then a fifth magnitude greater than the fourth magnitude is applied.

Table 2 illustrates a mixing setting similar to Table 1, but the direction of the motor is switched for each steady-state interval. Table 2 also differs in that the steady-state intervals are each 150 ms and the transient intervals are each 10 ms.

TABLE 2

| | Time (ms) | | | | | | | | |
|---|---|---|---|---|---|---|---|---|---|
| | 0 | 150 | 160 | 310 | 320 | 470 | 480 | 530 | 540 | 700 |
| PWM (%) | 15 | 0 | −16 | 0 | 17 | 0 | −18 | 0 | 19 | 0 |

It has been determined that lower PWM settings can cause pipette 62 to move with a linear oscillation or else move in a circular or elliptical motion of insufficient amplitude to disperse the paramagnetic particles within the fluid, whereas higher PWM settings can cause pipette 62 to rotate with sufficient amplitude. With a setting that causes pipette 62 to rotate with sufficient amplitude, a positive PWM causes pipette 42 to sweep in one direction, while a negative PWM causes pipette 42 to sweep in an opposite direction. By reversing motor 72, the control unit can therefore enhance mixing within cuvette 50.

In Table 2, for example, the positive PWM causes pipette 62 to sweep in a clockwise direction, and the negative PWM causes pipette 62 to sweep in a counter-clockwise direction. At 0 ms, the process begins by applying a 15% PWM while operating motor 72 in a first mode to cause pipette 62 to rotate in a clockwise direction. Pipette 62 is then transient from the 150 ms mark to the 160 ms mark, and then the PWM is raised to 16% at the 120 ms mark. Motor 72 is operated in reverse in the second steady-state interval to cause the pipette to rotate in the opposite direction as compared to the first steady-state interval. As shown in Table 2, the PWM is continuously increased 1% for each steady-state interval, and the sweeping direction of pipette 62 is alternated for each steady-state interval.

In an embodiment, in Table 2, a first vibrational magnitude is applied by motor 72, then a transient interval occurs, then a second magnitude greater than the first magnitude is applied while operating motor 72 in reverse, then a transient interval occurs, then a third magnitude greater than the second magnitude is applied, then a transient interval occurs, then a fourth magnitude greater than the third magnitude is applied while operating motor 72 in reverse, then a transient interval occurs, and then a fifth magnitude greater than the fourth magnitude is applied.

Table 3 illustrates a mixing setting without transient intervals and where the PWM is steadily increased and then decreased at the 600 ms mark.

TABLE 3

| | Time (ms) | | | | | | |
|---|---|---|---|---|---|---|---|
| | 0 | 120 | 240 | 360 | 480 | 600 | 700 |
| PWM (%) | 14 | 15 | 16 | 17 | 18 | 15 | 0 |

In Table 3, the steady-state intervals are each 120 ms and there are no transient intervals. At 0 ms, the process begins by applying a 14% PWM, and then the PWM applied by motor 72 is increased 1% at each 120 ms mark until 600 ms when it is dropped back down to 15%.

In an embodiment, in Table 3, a first vibrational magnitude is applied by motor 72, then a second magnitude greater than the first magnitude is applied, then a third magnitude greater than the second magnitude is applied, then a fourth magnitude greater than the third magnitude is applied, then a fifth magnitude greater than the fourth magnitude is applied, and then a sixth magnitude less than the third, fourth and fifth magnitudes and equal to the second magnitude is applied. In an alternative embodiment, the final or sixth magnitude can be equal to or less than any one of the first, second, third, fourth or fifth magnitudes.

Table 4 illustrates a mixing setting in which the PWM of motor 72 of vibrational assembly 66 alternates between transient and steady-state intervals, with the steady-state intervals alternating increases and decreases of the PWM.

TABLE 4

| | Time (ms) | | | | | | | |
|---|---|---|---|---|---|---|---|---|
| | 0 | 130 | 140 | 270 | 280 | 410 | 420 | 550 | 560 |
| PWM (%) | 15 | 0 | 12 | 0 | 14 | 0 | 13 | 0 | 16 |

In Table 4, the steady-state intervals are each 130 ms and the transient intervals are each 10 ms. At 0 ms, the process begins by applying a 15% PWM. Pipette 62 is then transient from the 130 ms mark to the 140 ms mark, and the PWM is lowered to 12% at the 140 ms mark. Pipette 62 is then transient from the 270 ms mark to the 280 ms mark, and the PWM is raised to 14% at the 280 ms mark.

In an embodiment, in Table 4, a first vibrational magnitude is applied by motor 72, then a transient interval occurs, then a second magnitude less than the first magnitude is applied, then a transient interval occurs, then a third magnitude greater than the second magnitude but less than the first magnitude is applied, then a transient interval occurs, then a fourth magnitude greater than the second magnitude but less than the first and third magnitudes is applied, then a transient interval occurs, and then a fifth magnitude greater than the first, second, third and fourth magnitudes is applied. Another way to describe the stead-state intervals of Table 4 is that the PWM is raised and lowered in alternating steady-state intervals.

Table 5 illustrates a mixing setting similar to Table 4, but the direction of motor 72 is switched for each steady-state interval.

TABLE 5

| | Time (ms) | | | | | | | |
|---|---|---|---|---|---|---|---|---|
| | 0 | 130 | 140 | 270 | 280 | 410 | 420 | 550 | 560 |
| PWM (%) | 15 | 0 | -12 | 0 | 14 | 0 | -13 | 0 | 16 |

In an embodiment, in Table 5, a first vibrational magnitude is applied by motor 72, then a transient interval occurs, then a second magnitude less than the first magnitude is applied while operating motor 72 in reverse, then a transient interval occurs, then a third magnitude greater than the second magnitude but less than the first magnitude is applied, then a transient interval occurs, then a fourth magnitude greater than the second magnitude but less than the first and third magnitudes is applied while operating motor 72 in reverse, then a transient interval occurs, and then a fifth magnitude greater than the first, second, third and fourth magnitudes is applied.

It has been determined that good mixing occurs for this embodiment when steady-state intervals are interspaced with transient intervals in which motor 72 of vibrational assembly 66 is not operated or operates at 0 PWM. It has also been determined that good mixing occurs when motor 72 is reversed in alternating steady-state intervals, and when the magnitude of the motor is raised and then lowered in alternating steady-state intervals as shown in Tables 4 and 5 above.

In an embodiment, the effective input voltage of motor 72 can be increased to motor 72 to raise the vibrational magnitude applied by motor 72, and the effective input voltage of motor 72 can be decreased to motor 72 to lower the vibrational magnitude applied by motor 72.

The control unit can store any one or more of the above mixing settings or other settings and cause motor 72 to be operated according to the mixing settings by varying the voltage sent to motor 72. By storing mixing settings, motor 72 does not need to be calibrated during installation and/or over its life.

The above mixing settings have been described as being applied by a pipette 62 that also injects fluid into the cuvette 50. It should be understood however that a pipette is only one type of mixing mechanism that can be vibrated according to the mixing settings described herein. Those of ordinary skill in the art will recognize other mixing mechanisms that can be vibrated according to the mixing settings described herein, for example, a stirring rod.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. An immunochemistry analysing system comprising:
   a source of paramagnetic particles;
   a source of fluid;
   at least one cuvette configured to receive the paramagnetic particles from the source of paramagnetic particles and the fluid from the source of fluid;
   at least one pipette configured to (i) translate so that at least a portion of the at least one pipette is located within the at least one cuvette and (ii) dispense at least one of the paramagnetic particles from the source of paramagnetic particles and the fluid from the source of fluid into the at least one cuvette so that the paramagnetic particles and the fluid can be mixed within the cuvette;
   at least one motor configured to move the at least one pipette while at least a portion of the at least one pipette is located in the at least one cuvette; and
   a control unit configured to vary a motor drive of the at least one motor using alternating transient and steady-state intervals to cause the at least one pipette to mix the fluid with the paramagnetic particles within the cuvette,
   wherein the motor drive causes the at least one pipette to vibrate during the steady-state intervals and stop vibrating during the transient intervals.

2. The immunochemistry analysing system of claim 1, wherein the at least one motor moves the at least one pipette by vibrating the at least one pipette.

3. The immunochemistry analysing system of claim 1, wherein the control unit is configured to reverse the motor at least one time to mix the fluid with the paramagnetic particles within the cuvette.

4. The immunochemistry analysing system of claim 1, wherein the control unit is configured to vary the motor drive of the at least one motor by increasing a magnitude of the motor drive of the at least one motor at least one time.

5. The immunochemistry analysing system of claim 1, wherein the control unit is configured to vary the motor drive of the at least one motor by decreasing a magnitude of the motor drive of the at least one motor at least one time.

6. The immunochemistry analysing system of claim 1, wherein the source of fluid includes at least one of a patient sample, a capture reagent and a rinse buffer.

7. An immunochemistry analysing system comprising:
   a source of paramagnetic particles;
   a cuvette configured to receive paramagnetic particles from the source of paramagnetic particles;
   a mixing mechanism configured to be at least partially submerged within the cuvette;
   a motor configured to vibrate the mixing mechanism;
   a memory storing at least one mixing setting in which a motor drive of the motor is varied over a series of time intervals; and
   a control unit configured to operate the motor according to the at least one mixing setting to cause the mixing mechanism to mix the paramagnetic particles within the cuvette,
   wherein the at least one mixing setting includes instructions to operate the motor using alternating transient and steady-state intervals.

8. The immunochemistry analysing system of claim 7, wherein the mixing mechanism is a pipette configured to dispense fluid into the cuvette to be mixed with the paramagnetic particles.

9. The immunochemistry analysing system of claim 7, wherein the mixing mechanism is a pipette configured to dispense the paramagnetic particles into the cuvette.

10. The immunochemistry analysing system of claim 7, wherein the at least one mixing setting includes instructions to increase a magnitude of the motor drive of the motor during the steady-state intervals.

11. The immunochemistry analysing system of claim 7, wherein the at least one mixing setting includes instructions to increase a magnitude of the motor drive of the motor during one steady-state time interval and decrease a magnitude of the motor drive of the motor during another steady-state time interval.

12. The immunochemistry analysing system of claim 7, wherein the at least one mixing setting includes instructions to reverse the motor during at least one of the steady-state time intervals.

13. A fluid mixing system comprising:
    a cuvette;
    a mixing mechanism configured to be at least partially submerged within the cuvette;
    a motor configured to vibrate the mixing mechanism;

a memory storing at least one mixing setting in which a motor drive of the motor is varied over a series of time intervals; and a control unit configured to operate the motor according to the at least one mixing setting to cause the mixing mechanism to mix a substance within the cuvette, wherein the at least one mixing setting includes instructions to operate the motor using alternating transient and steady-state intervals.

14. The fluid mixing system of claim 13, wherein the mixing mechanism includes a pipette configured to dispense fluid into the cuvette to be mixed with the substance.

15. The fluid mixing system of claim 13, wherein the at least one mixing setting includes instructions to increase a magnitude of the motor drive of the motor during the steady-state intervals.

16. The fluid mixing system of claim 13, wherein the at least one mixing setting includes instructions to increase a magnitude of the motor drive of the motor during one steady-state time interval and decrease a magnitude of the motor drive of the motor during another steady-state time interval.

17. The fluid mixing system of claim 13, wherein the at least one mixing setting includes instructions to reverse the motor during at least one of the steady-state time intervals.

\* \* \* \* \*